Figure 1:
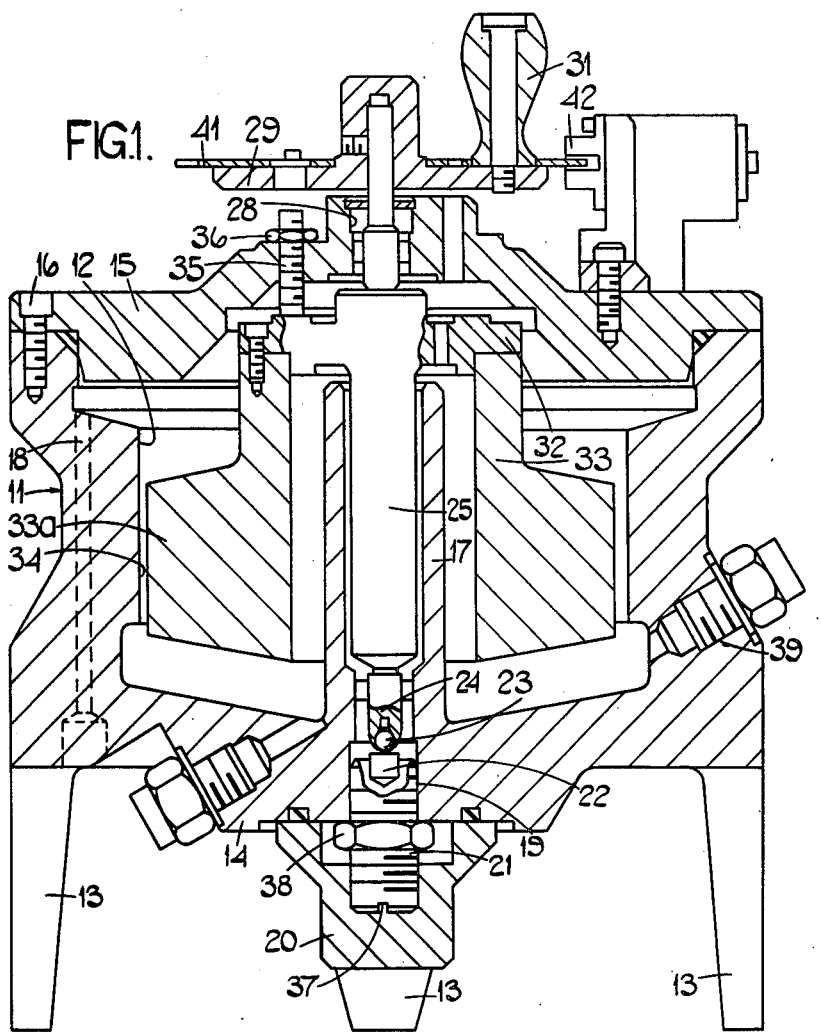

United States Patent [19]
Sivill

[11] 4,144,745
[45] Mar. 20, 1979

[54] VISCOMETER

[75] Inventor: Alistair D. Sivill, Birmingham, England

[73] Assignee: Lucas Industries Limited, Birmingham, England

[21] Appl. No.: 871,405

[22] Filed: Jan. 23, 1978

[30] Foreign Application Priority Data

Jan. 28, 1977 [GB] United Kingdom ............... 3471/77

[51] Int. Cl.² ........................................... G01N 11/14
[52] U.S. Cl. ................................................. 73/59
[58] Field of Search ............................ 73/59, 60, 54

[56] References Cited
U.S. PATENT DOCUMENTS

| | | | |
|---|---|---|---|
| 1,893,749 | 1/1933 | Klopsteg | 73/59 |
| 2,533,213 | 12/1950 | Barnard et al. | 73/59 |
| 2,573,505 | 10/1951 | Steffens | 73/59 |
| 2,709,363 | 5/1955 | Lea | 73/59 X |

*Primary Examiner*—Richard C. Queisser
*Assistant Examiner*—Joseph W. Roskos
*Attorney, Agent, or Firm*—Holman & Stern

[57] ABSTRACT

A Viscometer includes a casing defining therein a chamber and a rotor mounted in the chamber so as to define with the walls of the chamber a space for receiving the liquid whose viscosity is to be measured. Bearing means is interposed between the casing and the rotor is capable of rotational movement about an axis thereof relative to the casing, and means is operable to monitor the deceleration of the rotor when the rotor is rotating under the action of stored kinetic energy against the viscous drag of said liquid, the monitoring means being responsive to at least two of the three variables time, angular distance travelled by the rotor, and angular speed of the rotor.

9 Claims, 2 Drawing Figures

VISCOMETER

This invention relates to a viscometer.

A viscometer, according to the invention, includes a casing defining therein a chamber, a rotor mounted in the chamber so as to define with the walls of the chamber a space for receiving the liquid whose viscosity is to be measured, bearing means interposed between the casing and the rotor so that the rotor is capable of rotational movement about an axis thereof relative to the casing, and means for monitoring the deceleration of the rotor when the rotor is rotating under the action of stored kinetic energy against the viscous drag of said liquid, said means being responsive to at least two of the three variables time, angular distance travelled by the rotor, and angular speed of the rotor.

Preferably, said rotor defines an annular space with the chamber walls.

It is to be understood that the output from said monitoring means can be used to derive the absolute viscosity, $\mu$, of the liquid since the viscous torque $T_v$, generated by a rotating circular cylinder of radius R immersed in the liquid to define an annular column of liquid of height h and radial width c and rotating at an angular speed w is given by the equation:

$$T_v = 2\pi R^3 hw\mu/C$$

but R, h and c are constants of the apparatus concerned, so that $$T_v = Kw\mu$$

Moreover, the effect of this torque on the rotor is given by:

$$T_v = -I(dw/dt)$$

where I is the polar moment of inertia of the rotor and t is time so that:

$$Kw\mu + Idw/dt = 0$$

Solving this differential equation gives:

$$\theta = A \exp(-K\mu ht/I) + B$$

so that $w = -(Ak\mu h/I) \exp(-K\mu ht/I)$
where A and B are constants, and $\theta$ is the angular distance travelled by the rotor.

Considering the set of initial conditions, $t=0$, $\theta=0$ and $w=W_s$ (angular velocity at the start of a test), the values for A and B are as follows:

$$A = -I\, W_s/k\mu h$$
$$B = I\, W_s/k\mu h$$

Thus, when $t=T$ and $\theta=\Psi$ $$\Psi = (IW_s/k\mu h)[1 - \exp(-hk\mu T/I)]$$

It will therefore be appreciated that $\mu$ can be calculated by measuring the time (T) taken for the rotor to pass through a given angle ($\Psi$) while decelerating from speed $W_s$, or by measuring the angle ($\Psi$) moved by the rotor in decelerating for a given time (T) from a given speed $W_s$.

Alternatively, using the set of end conditions, $t=T$ and $w=W_e$ (angular velocity at the end of a test) the following equation:

$$W_e = W_s \exp(-k\mu hT/I)$$

can be derived. Hence $\mu$ may be calculated by measuring the time (T) taken for the rotor speed to fall from a given starting value, $W_s$, to a given end value, $W_e$; or by measuring the speed $W_e$ of the rotor after a given time (T) from a starting speed of $W_s$.

A further alternative set of boundary conditions may be used, e.g. when $\theta=\Psi$ and $w=W_e$ when the equation:

$$\Psi = IW_s/hk\mu[1 - (W_e/W_s)]$$

can be derived. Hence $\mu$ may be calculated by measuring the angle ($\Psi$) moved by the rotor when falling from a given starting speed of $W_s$, to a given final speed of $W_e$; or measuring the end speed $W_e$ from a given starting speed of $W_s$ when the rotor has moved through a given angle $\Psi$.

Figure 2:
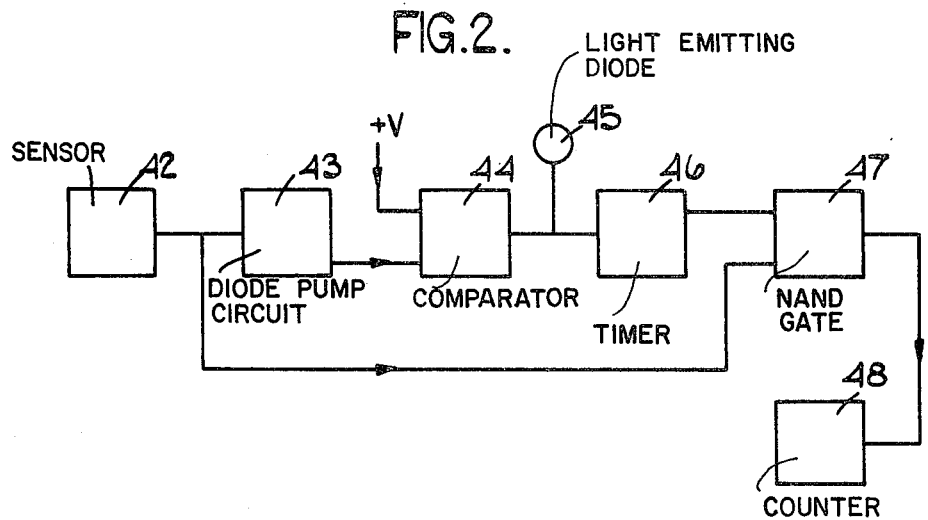

The invention will now be more particularly described with reference to the accompanying drawings in which:

FIG. 1 is a sectional view of a viscometer according to one example of the invention, and FIG. 2 is a block diagram of a circuit for monitoring the deceleration of the rotor of the viscometer shown in FIG. 1.

Referring to FIG. 1, the viscometer includes a casing 11 which defines a stepped cylindrical chamber 12 of generally circular cross-section and which is mounted on legs 13 so that, in use, the axis of the chamber 12 extends vertically. At one end, the chamber 12 is closed by an end wall 14 of the casing while its opposite end is closed by a lid 15 secured to the casing by screws 16 (only one shown). Formed integrally with the end wall 14 is a hollow cylindrical spigot 17 which extends coaxially within the chamber so that its free end lies above the level where a conduit 18 opens into the chamber. As will become apparent below, the level at which the conduit 18 enters the chamber 12 determines the liquid level in the chamber when the viscometer is in operation and hence in use the free end of the spigot lies above the level of liquid in the chamber.

Communicating with the bore in the spigot 17 is a screw-threaded hole 19 formed in the end wall 14 and receiving one end of a complementary screw-threaded plug 21, the other end of which mates with a transparent nut 20 for sealing the hole 19. Located in said one end of the plug 21 is a fixed bearing member 22 on which a ball bearing 23 is rotatably mounted, the ball bearing 23 being rigidly supported in a holder 24 which is defined at one end of a drive shaft 25 and which is journalled via an instrument ball bearing in the spigot 17. At its opposite end the drive shaft extends an aperture 28 in the lid 15, and is journalled in the aperture 28 via an instrument ball bearing, the end of the shaft 25 projecting from the lid being of non-circular cross section and being received in a complementary, centrally disposed bore in a drive wheel 29. The drive wheel 29 is provided with a handle 31 so that, in use, the wheel can be turned by hand to impart rotational movement to the drive shaft 25.

Intermediate its ends, the drive shaft 25 defines an integral flange 32 which is located a short distance above the free end of the spigot 18 and which is secured by screws to one end of a hollow cylindrical rotor 33 extending around and co-axial with the spigot 17. The rotor 33 is of generally circular cross-section but is stepped outwardly adjacent its opposite end to define a wide portion 33a which defines an annular space 34 with the cylindrical wall of the chamber 12. In use, the space 34 is filled with the liquid whose viscosity is to be measured. Moreover the radial width of the space 34 is arranged to be small compared with the distance between the narrow portion 33b of the rotor 33 and the cylindrical wall of the chamber 12 and with the distance between said opposite end of the rotor 33 and the end wall 14. Thus, when the rotor 33 is rotating in the liquid whose viscosity is to be measured, the drag experienced by the rotor is determined substantially entirely by the viscous torque on the portion 33a, with the viscous torque on the remainder of the rotor being negligible.

Mounted in a screw-threaded aperture in the lid 15 is an end play adjusting bolt 35 for the rotor 33. The bolt 35 is normally held captive by a nut 36 so that one end of the bolt is spaced a short distance from the rotor whereby the rotor is free to move relative to the bolt. However, on releasing the nut 36, said one end of the bolt can be brought into engagement with the rotor 33 to restrain the rotor against the axial movement which could, for example, occur during transport of the viscometer. In this respect it is also to be appreciated that the rotor 33 does not undergo axial movement when it is rotating during measurement of the viscosity of a liquid under test.

At its end projecting from the hole 19, the plug 21 is formed with a groove 37 adapted to receive a screwdriver so that, after removal of the nut 20 and release of a lock nut 38, the plug can be rotated in the hole 19 to vary the axial position of the rotor 33 and hence the height of the space 34. Moreover, since the nut 20 is transparent, any liquid which, in use, spills over into the bore in the spigot 17 forms a visible pool in the interior of the nut and can be drained by removal of the nut. In this respect, it is to be appreciated that it is desirable to maintain the bearing assembly 22, 23 free from the liquid under test since, with some liquids, this would result in a solid deposit building up on the bearing assembly thereby increasing the friction in the assembly.

When it is required to measure the viscosity of a liquid, the liquid is introduced into the chamber 12 by way of a filling aperture 39 in the casing 11, the supply of liquid being terminated when it overflows through the conduit 18. The arrangement is such that the annular space 34 is then filled with the liquid under test. The handle 31 is then turned to rotate the drive wheel 29 and rotor 33 above a given angular velocity ($W_s$), whereupon the handle is released so that the rotor thereafter moves under the action of its stored kinetic energy. This movement of the rotor 33 is opposed by the viscous drag of the liquid on the portion 33a so that the rotor gradually decelerates in a manner determined by the appropriate equation given above. Thus, when the angular velocity of the rotor falls to said given value ($W_s$), the deceleration of the rotor is monitored so that the viscosity of the liquid can be determined. In the example shown, this is effected by means of a toothed disc 41 which moves with the wheel 29 past a fixed, photoelectric sensor 42 so as to generate pulses in the sensor which are then fed to the circuit shown in FIG. 2.

Referring to FIG. 2, the pulses from the sensor 42 have a frequency proportional to the angular velocity of the rotor 33 and are fed to a diode pump circuit 43 which produces a d.c. voltage proportional to the frequency of the pulses. This d.c. voltage is then applied to a comparator 44 which is in the form of the integrated circuit component supplied by Signetics as type NE532 and which is arranged to switch when the applied voltage equals a preset voltage V corresponding to said predetermined angular speed of the rotor 33. The output from the comparator 44 is fed to a light-emitting diode 45 and a timer 46 which is in the form of the integrated circuit component supplied by Signetics as type NE555 and which has a preset time period, conveniently of 8 seconds. The output from the timer 46 is fed to one input of a Schmitt NAND gate 47 in the form of the integrated circuit component supplied by Texas Instruments Ltd., as type SN7413, the other input of the gate 47 being fed from the sensor 42. The output from the gate 47 is fed to a digital counter 48.

In use, when the rotor 33 is rotated above said predetermined angular velocity, the comparator 44 produces an output which is arranged to energise the diode 45 and at this stage the counter 48 must be reset to zero. On release of the rotor, its angular velocity gradually falls until said predetermined value is reached at which point the comparator 44 switches to trigger the timer 46 which then applies a voltage to said one input of the gate 47. When this occurs, the gate 47 opens to feed pulses to the counter 48 until the preset time period of the timer 46 expires and the gate is closed. The resultant reading of the counter 48 indicates the number of pulses generated in the sensor 42 during said preset time period by the disc 41 and is therefore a measure of the distance travelled by the decelerating rotor 33 in said time period. Thus, when the apparatus has been standardised to allow calculation of the constant K, the counter reading can be used to determine the viscosity of the liquid under test.

The apparatus described above is particularly intended for use with low viscosity materials (typically less than 50 cp) where direct measurement of absolute viscosity is difficult. In one practical embodiment of such apparatus, the rotor 33 was formed of Dural and had a diameter of 80 mm so as to define an annular space 34 of radial width 2mm and height 30mm. The disc 41 was arranged to have 60 teeth and, in measuring the viscosity of a given liquid, said predetermined angular velocity was arranged to be 120 r.p.m. Moreover, when the rotor speed fell to this predetermined value, the movement of the rotor was monitored over 8 seconds. Using this arrangement, counter readings of 905, 810 and 732 were obtained with distilled water, n-butyl and analine respectfully.

As an alternative to the arrangement described above, the space used to measure the viscous drag imparted by different liquids on a rotor can be defined between an axial end of the rotor and the end wall of a cylindrical chamber. The annular space employed in the above example is, however, preferred.

I claim:

1. A viscometer including a casing defining therein a chamber, a rotor mounted in the chamber so as to define with the walls of the chamber a space for receiving the liquid whose viscosity is to be measured, bearing means interposed between the casing and the rotor so that the rotor is capable of rotational movement about an axis thereof relative to the casing, and means for monitoring the deceleration of the rotor when the rotor is rotating under the action of stored kinetic energy against the viscous drag of said liquid, said means being responsive to at least two of the three variables time, angular distance travelled by the rotor, and angular speed of the rotor.

2. A viscometer as claimed in claim 1, wherein the chamber and the rotor include cylindrical portions which are co-axial and of generally circular cross-section, said space being defined between said cylindrical portions and being annular.

3. A viscometer as claimed in claim 2 including means shrouding said bearing means so that, in use, said bearing means is isolated from the liquid received in said space.

4. A viscometer as claimed in claim 3, wherein said shrouding means includes a hollow spigot projecting from the casing and rotatably supporting one end of a drive shaft for the rotor.

5. A viscometer as claimed in claim 4, wherein the other end of said drive shaft is coupled to a handle for imparting rotational movement to the rotor.

6. A viscometer as claimed in claim 1 including means shrouding said bearing means so that, in use, said bearing means is isolated from the liquid received in said space.

7. A viscometer as claimed in claim 6, wherein said shrouding means includes a hollow spigot projecting from the casing and rotatably supporting one end of a drive shaft for the rotor.

8. A viscometer as claimed in claim 7, wherein the other end of said drive shaft is coupled to a handle for imparting rotational movement to the rotor.

9. A method of measuring the viscosity of liquid with a viscometer having a casing defining a chamber, a rotor mounted in said chamber so as to define with the walls of the chamber a space for receiving said liquid, said method comprising the following steps of:
 (a) introducing the liquid into a viscometer, so as to fill said space with the liquid, then
 (b) rotating the rotor above a predetermined angular velocity, then
 (c) allowing the rotor to rotate under the action of its stored kinetic energy and against the viscous drag of the liquid; and
 (d) when the angular velocity of the rotor during said allowing step falls to said predetermined velocity, monitoring the deceleration of the rotor by measuring at least two of the three variables time, angular distance travelled by the rotor, and angular speed of the rotor.

* * * * *